US00PP35097P2

(12) United States Plant Patent
Flore

(10) Patent No.: US PP35,097 P2
(45) Date of Patent: Apr. 11, 2023

(54) ***PHALAENOPSIS* PLANT NAMED 'MI01930'**

(50) Latin Name: *Phalaenopsis hybrida*
Varietal Denomination: MI01930

(71) Applicant: MICROFLOR N.V., Lochristi (BE)

(72) Inventor: Febe Flore, Lochristi (BE)

(73) Assignee: MICROFLOR N.V., Lochristi (BE)

( * ) Notice: Subject to any disclaimer, the term of this patent is extended or adjusted under 35 U.S.C. 154(b) by 0 days.

(21) Appl. No.: 17/827,938

(22) Filed: May 30, 2022

(51) Int. Cl.
*A01H 5/02* (2018.01)
*A01H 6/62* (2018.01)

(52) U.S. Cl.
USPC ..... Plt./311
CPC ..... *A01H 6/62* (2018.05); *A01H 5/02* (2013.01)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'MI01930', characterized by its upright plant habit; vigorous growth habit and rapid growth rate; strong flowering stems; numerous strong leaves; freely flowering habit with typically two inflorescences per plant, each inflorescence with numerous flowers; soft pink-colored flowers; and good postproduction longevity.

1 Drawing Sheet

Figure 1:
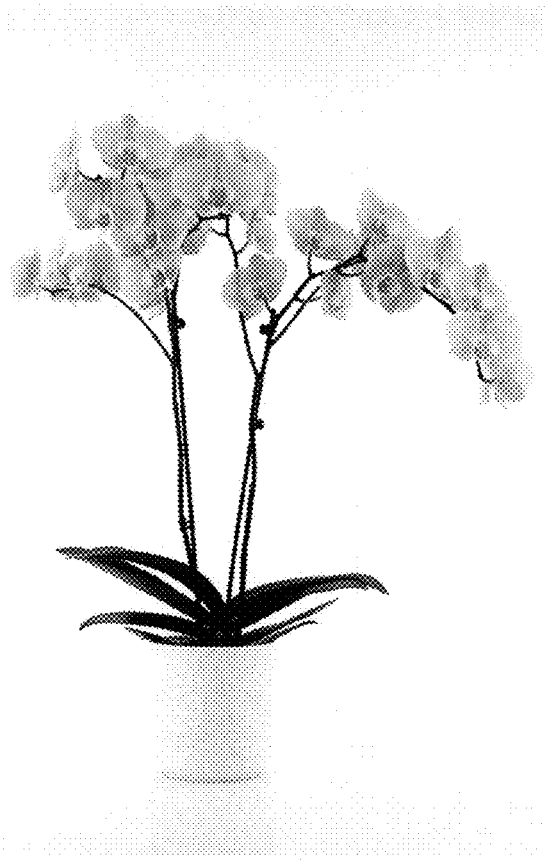

Botanical designation: *Phalaenopsis hybrida.*
Cultivar denomination: 'MI01930'.

STATEMENT REGARDING PRIOR DISCLOSURES BY INVENTOR/APPLICANT & ASSIGNEE

An European Union Plant Breeder's Rights application for the instant plant was filed by the Assignee, Microflor N.V. of Lochristi, Belgium on Mar. 8, 2022, application number 2022/0622 and was published on Jun. 15, 2022. Foreign priority is not claimed to this application.

The Inventor and Applicant/Assignee assert that no publications nor advertisements relating to sales, offers for sale or public distribution occurred more than one year prior to the effective filing date of this U.S. Plant Patent application. Any information about the claimed plant would have been obtained from a direct or indirect disclosure from the Inventor or the Applicant/Assignee. Inventor and Applicant/Assignee claim a prior art exception under 35 U.S.C. 102 (b)(1) for disclosure and/or sales prior to the filing date but less than one year prior to the effective filing date of this U.S. Plant Patent application.

BACKGROUND OF THE INVENTION

The present invention relates to a new and distinct cultivar of *Phalaenopsis* plant, botanically known as *Phalaenopsis hybrida*, and hereinafter referred to by the name 'MI01930'.

The new *Phalaenopsis* plant is a product of a planned breeding program conducted by the Inventor in Lochristi, Belgium. The objective of the breeding program is to develop new freely flowering *Phalaenopsis* plants with good leaf shape and relatively large flowers with unique and attractive flower coloration.

The new *Phalaenopsis* plant originated from a cross-pollination by the Inventor in September, 2014 in Lochristi, Belgium of a proprietary selection of *Phalaenopsis hybrida* identified as code number MI00019, not patented, as the female, or seed, parent with a proprietary selection of *Phalaenopsis hybrida* identified as code number PH02453, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in June, 2017.

Asexual reproduction of the new *Phalaenopsis* plant by in vitro meristem propagation in a controlled environment in Lochristi, Belgium since October, 2018 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI01930'. These characteristics in combination distinguish 'MI01930' as a new and distinct *Phalaenopsis* plant:

1. Upright plant habit.
2. Vigorous growth habit and rapid growth rate.
3. Strong flowering stems.
4. Numerous strong leaves.
5. Freely flowering habit with typically two inflorescences per plant, each inflorescence with numerous flowers.
6. Soft pink-colored flowers.
7. Good postproduction longevity.

Plants of the new *Phalaenopsis* can be compared to plants of the female parent selection. Plants of the new *Phalaen-*

*opsis* differ primarily from plants of the female parent selection in the following characteristics:

1. Plants of the new *Phalaenopsis* are shorter than plants of the female parent selection.
2. Plants of the new *Phalaenopsis* grow faster than plants of the female parent selection.
3. Plants of the new *Phalaenopsis* have more leaves per plant than plants of the female parent selection.
4. Flowers of plants of the new *Phalaenopsis* are lighter pink in color than flowers of plants of the female parent selection.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* have more inflorescences per plant than plants of the male parent selection.
2. Flowers of plants of the new *Phalaenopsis* last seven weeks longer than flowers of plants of the male parent selection.

Plants of the new *Phalaenopsis* can be compared to plants of *Phalaenopsis hybrida* 'Kikion', not patented. In side-by-side comparisons, plants of the new *Phalaenopsis* differ primarily from plants of 'Kikion' in the following characteristics:

1. Plants of the new *Phalaenopsis* have larger flowers than plants of 'Kikion'.
2. Flowers of plants of the new *Phalaenopsis* are darker pink in color than flowers of plants of 'Kikion'.
3. Flowers of plants of the new *Phalaenopsis* have smaller spots on the lateral lobes of the labellum than flowers of plants of 'Kikion'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph at the top of the sheet (FIG. 1) is a side perspective view of a typical flowering plant of 'MI01930' grown in a container.

Figure 2:
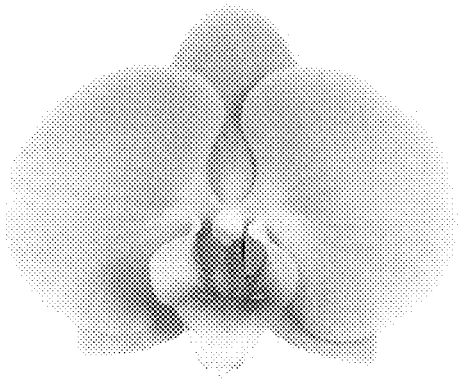

The photograph at the bottom of the sheet (FIG. 2) is a close-up view of a typical flower of 'MI01930'.

DETAILED BOTANICAL DESCRIPTION

The aforementioned photographs and following observations and measurements describe plants grown during the winter in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/m$^2$ to 375 Watt/m$^2$. Plants were 69 weeks old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI01930'.

Parentage:

*Female parent*.—Proprietary selection of *Phalaenopsis hybrida* identified as code number MI00019, not patented.

*Male parent*.—Proprietary selection of *Phalaenopsis hybrida* identified as code number PH02453, not patented.

Propagation:

*Type*.—By in vitro meristem propagation.

*Time to initiate roots, summer*.—About nine to ten weeks at temperatures about 26° C.

*Time to initiate roots, winter*.—About ten to eleven weeks at temperatures about 26° C.

*Time to produce a rooted young plant, summer*.—About 140 to 160 days at temperatures about 26° C.

*Time to produce a rooted young plant, winter*.—About 150 to 180 days at temperatures about 26° C.

*Root description*.—Thick, fleshy; typically grey green in color, with some anthocyanin at the root tips; actual color of the roots is dependent on substrate composition, water quality, fertilizer, substrate temperature and age of roots.

*Rooting habit*.—Small amount of branching; sparse.

Plant description:

*Plant form and growth habit*.—Herbaceous epiphyte; upright plant habit with typically two inflorescences per plant, each inflorescence with numerous flowers; monopodial; vigorous growth habit and rapid growth rate.

*Plant height, substrate level to top of foliar plane*.—About 19 cm.

*Plant height, substrate level to top of inflorescences*.—About 50 cm.

*Plant diameter or spread*.—About 59 cm.

Leaf description:

*Arrangement and quantity*.—Distichous, simple; sessile; about nine leaves per plant.

*Length*.—About 25 cm.

*Width*.—About 8.1 cm.

*Aspect*.—Semi-erect to almost horizontal.

*Shape*.—Oblanceolate.

*Apex*.—Unequal acute.

*Base*.—Sheathing.

*Margin*.—Entire.

*Texture and luster, upper and lower surfaces*.—Smooth, glabrous; moderately glossy.

*Venation pattern*.—Camptodromous.

*Color*.—When opening and fully expanded leaves, upper surface: Slightly darker than 137A; venation, close to 137A. When opening and fully expanded leaves, lower surface: Close to 137B; venation, close to 137B.

Inflorescence description:

*Appearance and flowering habit*.—Showy zygomorphic flowers arranged on axillary branched racemes; typically two inflorescences per plant; each inflorescence with about 23 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about 17 weeks after an inductive cooling period; flowers open about five weeks after flower buds develop.

*Flower longevity*.—Long flowering period, individual flowers maintain good substance for about 21 weeks on the plant; flowers not persistent.

*Inflorescence length* (*lowermost flower to inflorescence apex*).—About 39 cm.

*Inflorescence width*.—About 34 cm by 59 cm.

*Flower buds*.—Height: About 2 cm. Diameter: About 1.5 cm. Shape: Ovate. Color: Close to 165C with greenish tinge; distally, close to 64A.

*Flower diameter*.—About 9.2 cm.

*Flower depth*.—About 3.5 cm.

*Petals, quantity and arrangement*.—Three, two lateral petals and one center petal transformed into a labellum.

*Lateral petals*.—Length: About 4 cm. Width: About 5.1 cm. Shape: Reniform. Apex: Rounded. Margin: Entire. Texture and luster, upper and lower surfaces: Smooth, glabrous, velvety; matte. Color: When opening and fully opened, upper surface: Close to 76A; color does not change with subsequent development. When opening and fully opened, lower surface: Close to 76C with venation, close to 76A; color does not change with subsequent development.

*Labella*.—Appearance: Tri-lobed with two lateral lobes and a central lobe. Length: About 2.4 cm. Width: About 2 cm. Shape, lateral lobes: Obovate. Shape, central lobe: Triangular. Apex, lateral lobes: Obtuse. Apex, central lobe: Cleft with two long, narrow and recurved cirrose tips. Margins, lateral and central lobes: Entire. Texture and luster, upper and lower surfaces: Smooth, glabrous, moderately velvety; matte. Callosities: Located at the base of the labellum and attachment point of the lateral petals; about 5 mm in length, about 6 mm in width and about 6 mm in height. Color: When opening and fully opened, upper surface: Lateral lobes: Close to 69D; proximally, close to 163B; at the base, spots, close to 59B. Central lobe: Close to 76D. Callosities: Close to 14B; spots, close to 59B. When opening and fully opened, lower surface: Lateral lobes: Close to 76C. Central lobe: Close to 76B and 75A.

*Sepals*.—Quantity and arrangement: Three, two lower lateral sepals and one upper dorsal sepal. Length, lateral sepal: About 4.5 cm. Width, lateral sepals: About 2.9 cm. Length, dorsal sepal: About 4.1 cm. Width, dorsal sepal: About 2.9 cm. Shape, lateral sepals: Ovate. Shape, dorsal sepal: Elliptic. Apex, lateral sepals: Bluntly acute. Apex, dorsal sepal: Obtuse. Base, lateral and dorsal sepals: Acute to obtuse. Margin, lateral and dorsal sepals: Entire. Texture and luster, lateral and dorsal sepals, upper and lower surfaces: Smooth, glabrous, velvety; matte. Color, lateral sepals: When opening, upper surface: Close to 75A. When opening, lower surface: Close to 78D; towards the apex, close to 78B; venation, close to 78B. Fully opened, upper surface: Close to 76A. Fully opened, lower surface: Close to 76B. Color, dorsal sepal: When opening, upper surface: Close to 76A. When opening, lower surface: Close to 78D; towards the apex, close to 78B; venation, close to 78B. Fully opened, upper surface: Close to 76A. Fully opened, lower surface: Close to 76B.

*Peduncles*.—Length: About 77 cm. Diameter: About 7 mm. Strength: Strong, somewhat flexible. Aspect: Mostly upright. Texture and luster: Smooth, glabrous; matte. Color: Close to 147A; fine dots, close to 200C.

*Pedicels*.—Length: About 3.8 cm. Diameter: About 3 mm. Strength: Moderately strong. Aspect: About 85° from peduncle axis. Texture and luster: Smooth, glabrous; matte. Color: Close to between 146A and 147A; distally, tinged with close to 75A.

*Reproductive organs*.—Androecium: Column length: About 1 cm. Column width: About 6 mm. Column color: Close to 76D. Pollinia quantity: Two. Pollinia diameter (per two pollinia): About 3 mm. Pollinia color: Close to 24A. Gynoecium: Stigma length: About 5 mm. Stigma width: About 3 mm. Stigma shape: Reniform. Stigma color: Close to NN155D. Ovary length: About 1.2 cm. Ovary diameter: About 2 mm. Ovary color: Close to 75A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI01930' as illustrated and described.

* * * * *